(12) United States Patent
Leonard

(10) Patent No.: US 7,607,250 B2
(45) Date of Patent: Oct. 27, 2009

(54) AIR FRESHENER WITH PICTURE FRAME

(75) Inventor: Stephen B. Leonard, Franksville, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 389 days.

(21) Appl. No.: 11/118,500

(22) Filed: Apr. 29, 2005

(65) Prior Publication Data
US 2006/0000920 A1 Jan. 5, 2006

Related U.S. Application Data

(63) Continuation-in-part of application No. 10/880,634, filed on Jun. 30, 2004, now Pat. No. 7,188,780, and a continuation-in-part of application No. 10/881,816, filed on Jun. 30, 2004, now Pat. No. 7,213,770, and a continuation-in-part of application No. 10/880,885, filed on Jun. 30, 2004, now abandoned.

(51) Int. Cl.
A47G 1/06 (2006.01)

(52) U.S. Cl. ............................... 40/725; 40/765; 40/781

(58) Field of Classification Search ................ 40/781, 40/745, 725, 709, 722, 765, 766, 767, 649; 239/60, 55, 56, 53
See application file for complete search history.

(56) References Cited

U.S. PATENT DOCUMENTS

| 882,710 | A | 3/1908 | Pearsall |
| 886,840 | A | 5/1908 | Mueller |
| 1,068,621 | A | 7/1913 | Abraham |
| 1,204,934 | A | 11/1916 | Burford et al. |
| 1,261,133 | A | 4/1918 | Kidd |
| 1,802,999 | A | 4/1931 | Budd |
| 1,815,841 | A * | 7/1931 | Gastgivar ..................... 40/766 |
| 1,940,328 | A | 12/1933 | Schrotenboer |
| 2,268,529 | A | 12/1941 | Stiles |
| 2,469,656 | A | 5/1949 | Lienert |
| 2,550,954 | A | 5/1951 | Benedict |
| 2,577,320 | A | 12/1951 | Fenyo |
| 2,579,715 | A | 12/1951 | Wilson et al. |
| D169,871 | S | 6/1953 | Speer et al. |
| 2,779,624 | A | 1/1957 | Friedman |
| 2,785,490 | A * | 3/1957 | Fabry ......................... 40/711 |

(Continued)

FOREIGN PATENT DOCUMENTS

EP 0 645 081 7/2001

(Continued)

OTHER PUBLICATIONS htto://www.glade.com/piso.asp.

(Continued)

Primary Examiner—S. Joseph Morano
Assistant Examiner—Christopher E Veraa

(57) ABSTRACT

A picture frame having front and rear faces includes a recess disposed within the rear face of the frame. A dispenser is disposed within the recess of the rear face, wherein the dispenser includes a reservoir and a vapor permeable membrane. A slot is also disposed within a side wall of the frame that is configured to hold an image.

19 Claims, 11 Drawing Sheets

U.S. PATENT DOCUMENTS

| | | | |
|---|---|---|---|
| 2,840,689 A | 6/1958 | Kazor | |
| 3,178,844 A | 4/1965 | Christian | |
| 3,424,380 A | 1/1969 | Curran | |
| 3,540,146 A | 11/1970 | Watkins | |
| 3,558,055 A | 1/1971 | Storchheim | |
| 3,570,160 A | 3/1971 | Spertus | |
| 3,741,711 A | 6/1973 | Bryant | |
| 3,790,081 A | 2/1974 | Thornton et al. | |
| 3,804,330 A | 4/1974 | Miller, Jr. et al. | |
| 3,822,495 A | 7/1974 | Ohfuji | |
| 3,948,445 A | 4/1976 | Andeweg | |
| D243,402 S | 2/1977 | Irving | |
| 4,009,384 A | 2/1977 | Holland | |
| D247,573 S | 3/1978 | Schimanski | |
| 4,101,720 A | 7/1978 | Taylor et al. | |
| 4,157,787 A | 6/1979 | Schwartz | |
| 4,158,440 A | 6/1979 | Sullivan et al. | |
| 4,161,283 A | 7/1979 | Hyman | |
| 4,165,573 A | 8/1979 | Richards | |
| 4,170,080 A | 10/1979 | Bergh et al. | |
| 4,173,604 A | 11/1979 | Dimacopoulos | |
| 4,184,099 A | 1/1980 | Lindauer et al. | |
| 4,285,468 A * | 8/1981 | Hyman | 239/55 |
| D260,503 S | 9/1981 | Stangarone | |
| 4,293,095 A | 10/1981 | Hamilton et al. | |
| 4,314,915 A | 2/1982 | Wiegers et al. | |
| D263,334 S | 3/1982 | Schimanski | |
| 4,327,056 A | 4/1982 | Gaiser | |
| D269,838 S | 7/1983 | Altonaga | |
| 4,411,829 A | 10/1983 | Schulte-Elte et al. | |
| D271,359 S | 11/1983 | Le | |
| 4,434,306 A | 2/1984 | Kobayashi et al. | |
| D275,223 S | 8/1984 | Marxen | |
| D275,700 S | 9/1984 | Marxen | |
| 4,476,171 A | 10/1984 | Takeuchi | |
| 4,493,011 A | 1/1985 | Spector | |
| D279,146 S | 6/1985 | McCaffrey | |
| D280,363 S | 9/1985 | Wisecup, Jr. | |
| 4,549,250 A | 10/1985 | Spector | |
| 4,580,581 A | 4/1986 | Reece et al. | |
| D288,003 S | 1/1987 | Hoyt | |
| 4,634,614 A * | 1/1987 | Holzner | 428/34.2 |
| 4,695,435 A | 9/1987 | Spector | |
| 4,714,984 A | 12/1987 | Spector | |
| 4,720,409 A | 1/1988 | Spector | |
| D296,957 S | 8/1988 | Gordon et al. | |
| 4,762,275 A | 8/1988 | Herbert et al. | |
| 4,781,895 A | 11/1988 | Spector | |
| 4,794,714 A | 1/1989 | Weisgerber | |
| 4,809,912 A | 3/1989 | Santini | |
| 4,814,212 A | 3/1989 | Spector | |
| 4,849,606 A | 7/1989 | Martens, III et al. | |
| 4,874,129 A | 10/1989 | DiSapio et al. | |
| 4,883,692 A | 11/1989 | Spector | |
| D305,703 S | 1/1990 | Wang | |
| 4,898,328 A | 2/1990 | Fox et al. | |
| 4,913,349 A | 4/1990 | Locko | |
| 4,917,301 A | 4/1990 | Munteanu | |
| 4,921,636 A | 5/1990 | Traas | |
| 4,939,858 A | 7/1990 | Dailey | |
| 4,959,087 A | 9/1990 | Kappernaros | |
| 4,979,619 A * | 12/1990 | Hager | 206/509 |
| 4,993,177 A | 2/1991 | Hudson | |
| 4,995,555 A | 2/1991 | Woodruff | |
| D320,266 S | 9/1991 | Kunze | |
| 5,060,858 A | 10/1991 | Santini | |
| D325,077 S | 3/1992 | Kearnes | |
| 5,148,983 A | 9/1992 | Muniz | |
| 5,148,984 A | 9/1992 | Bryson et al. | |
| 5,163,616 A | 11/1992 | Bernarducci et al. | |
| 5,170,886 A | 12/1992 | Holzner | |
| 5,219,121 A | 6/1993 | Fox et al. | |
| 5,230,867 A | 7/1993 | Kunze et al. | |
| D339,238 S | 9/1993 | Hamilton | |
| D339,242 S | 9/1993 | Sontag et al. | |
| 5,247,745 A | 9/1993 | Valentino | |
| 5,259,555 A | 11/1993 | Kiefer | |
| 5,297,732 A | 3/1994 | Hahn | |
| D346,068 S | 4/1994 | White | |
| 5,304,358 A | 4/1994 | Hoyt et al. | |
| 5,334,361 A | 8/1994 | Rafaelides et al. | |
| 5,361,522 A * | 11/1994 | Green | 40/725 |
| 5,367,802 A | 11/1994 | Rosenberg | |
| D354,627 S | 1/1995 | Rowan | |
| 5,395,047 A | 3/1995 | Pendergrass | |
| 5,402,517 A | 3/1995 | Gillett et al. | |
| D358,037 S | 5/1995 | Monroe | |
| D360,461 S | 7/1995 | Gillespie | |
| 5,439,100 A | 8/1995 | Gordon et al. | |
| D361,896 S | 9/1995 | Bramley et al. | |
| 5,462,006 A | 10/1995 | Thiruppathi | |
| D366,107 S * | 1/1996 | Shaffer | D23/366 |
| 5,503,332 A | 4/1996 | Glenn | |
| D369,473 S | 5/1996 | Gluck | |
| 5,529,243 A | 6/1996 | Hoyt et al. | |
| D372,797 S | 8/1996 | Ilaria et al. | |
| 5,556,192 A | 9/1996 | Wang | |
| D374,777 S | 10/1996 | Agam | |
| D376,002 S | 11/1996 | Upson | |
| D376,420 S | 12/1996 | Rymer | |
| D376,914 S | 12/1996 | Waszkiewicz | |
| D380,822 S | 7/1997 | Decker et al. | |
| 5,647,052 A | 7/1997 | Patel et al. | |
| 5,651,942 A | 7/1997 | Christensen | |
| D383,613 S | 9/1997 | Handler | |
| D384,821 S | 10/1997 | Sugar | |
| 5,679,334 A | 10/1997 | Semoff et al. | |
| 5,711,955 A | 1/1998 | Karg | |
| 5,716,000 A | 2/1998 | Fox | |
| D392,031 S | 3/1998 | Miller | |
| D392,032 S | 3/1998 | Zaragoza et al. | |
| 5,735,460 A | 4/1998 | Eisenbraun | |
| 5,744,106 A | 4/1998 | Eagle | |
| 5,749,519 A | 5/1998 | Miller | |
| 5,749,520 A | 5/1998 | Martin et al. | |
| 5,782,409 A | 7/1998 | Paul | |
| 5,788,155 A | 8/1998 | Martin et al. | |
| 5,804,264 A | 9/1998 | Bowen | |
| D399,298 S | 10/1998 | Whitehead | |
| D401,767 S | 12/1998 | Leung | |
| 5,845,847 A | 12/1998 | Martin et al. | |
| D405,473 S | 2/1999 | Tikhonski et al. | |
| D405,961 S | 2/1999 | Stangl et al. | |
| 5,875,968 A | 3/1999 | Miller et al. | |
| 5,885,701 A | 3/1999 | Berman et al. | |
| D407,809 S | 4/1999 | Hammond | |
| 5,899,382 A | 5/1999 | Hayes et al. | |
| 5,950,922 A | 9/1999 | Flinn | |
| 5,961,043 A | 10/1999 | Samuelson et al. | |
| 5,975,427 A | 11/1999 | Harries | |
| 6,031,967 A | 2/2000 | Flashinski et al. | |
| D424,812 S | 5/2000 | Kacius | |
| 6,065,687 A | 5/2000 | Suzuki et al. | |
| 6,106,786 A | 8/2000 | Akahoshi | |
| 6,109,537 A | 8/2000 | Heath | |
| D431,075 S | 9/2000 | Barraclough | |
| 6,112,496 A | 9/2000 | Hugus et al. | |
| 6,144,801 A | 11/2000 | Lehoux et al. | |
| 6,152,379 A | 11/2000 | Sorgenfrey | |
| 6,154,607 A | 11/2000 | Flashinski et al. | |
| D435,100 S | 12/2000 | Pesu et al. | |
| D437,404 S | 2/2001 | Wu | |
| 6,205,692 B1 * | 3/2001 | Kite | 40/615 |
| D439,964 S | 4/2001 | Wu | |

| | | | |
|---|---|---|---|
| D441,441 S | 5/2001 | Upson | |
| D445,262 S | 7/2001 | Rowan | |
| 6,254,248 B1 | 7/2001 | McAuley et al. | |
| 6,254,836 B1 | 7/2001 | Fry | |
| D451,990 S | 12/2001 | Millet | |
| 6,328,935 B1 | 12/2001 | Buccellato | |
| D453,561 S | 2/2002 | Nelson | |
| 6,354,710 B1 | 3/2002 | Nacouzi | |
| 6,358,577 B1 | 3/2002 | Bowen et al. | |
| 6,363,734 B1 | 4/2002 | Aoyagi | |
| 6,367,706 B1 | 4/2002 | Putz | |
| D456,620 S | 5/2002 | Vincent | |
| D456,888 S | 5/2002 | Buthier | |
| D461,006 S | 7/2002 | Buthier | |
| D461,393 S | 8/2002 | Aubert | |
| 6,435,423 B2 | 8/2002 | Hurry et al. | |
| 6,478,440 B1 | 11/2002 | Jaworski et al. | |
| 6,484,425 B1 | 11/2002 | Hirsch | |
| 6,526,636 B2 | 3/2003 | Bernhardt | |
| 6,548,015 B1 | 4/2003 | Stubbs et al. | |
| 6,555,068 B2 | 4/2003 | Smith | |
| D476,726 S | 7/2003 | Rosenberg | |
| 6,610,254 B1 | 8/2003 | Furner et al. | |
| D479,742 S | 9/2003 | Hollingsworth | |
| 6,618,974 B2 | 9/2003 | Szalay | |
| 6,627,857 B1 | 9/2003 | Tanner et al. | |
| D480,221 S | 10/2003 | Luciano | |
| D481,113 S | 10/2003 | Groene et al. | |
| 6,631,852 B1 | 10/2003 | O'Leary | |
| 6,638,591 B2 | 10/2003 | Bowen et al. | |
| D481,785 S | 11/2003 | Koike | |
| 6,643,967 B1 | 11/2003 | Bloom | |
| 6,648,239 B1 | 11/2003 | Myny et al. | |
| 6,663,838 B1 | 12/2003 | Soller et al. | |
| D485,607 S | 1/2004 | Wu | |
| D487,308 S | 3/2004 | Engerant | |
| 6,705,541 B2 | 3/2004 | Schuehrer et al. | |
| 6,714,725 B2 | 3/2004 | Grone et al. | |
| 6,722,578 B2 | 4/2004 | Skalitzky et al. | |
| 6,730,311 B2 | 5/2004 | Maleeny et al. | |
| 6,749,672 B2 | 6/2004 | Lynn | |
| 6,790,436 B2 | 9/2004 | Williams et al. | |
| 6,808,791 B2 | 10/2004 | Curro et al. | |
| D498,524 S | 11/2004 | Morillas | |
| D498,525 S | 11/2004 | Harbutt et al. | |
| D498,836 S | 11/2004 | Morillas | |
| 6,826,863 B1 | 12/2004 | Goodfellow | |
| 6,839,506 B2 * | 1/2005 | He et al. | 392/392 |
| 6,998,581 B2 | 2/2006 | Currie | |
| 7,175,815 B2 | 2/2007 | Yamasaki et al. | |
| 2001/0030243 A1 | 10/2001 | Hurry et al. | |
| 2003/0007887 A1 | 1/2003 | Roumpos et al. | |
| 2003/0017129 A1 | 1/2003 | Maleeny et al. | |
| 2003/0089791 A1 | 5/2003 | Chen et al. | |
| 2003/0094503 A1 | 5/2003 | Rymer et al. | |
| 2003/0152374 A1 | 8/2003 | Grone et al. | |
| 2003/0200690 A1 | 10/2003 | Galloway | |
| 2004/0000596 A1 | 1/2004 | Cuthbert | |
| 2004/0057975 A1 | 3/2004 | Maleeny et al. | |
| 2004/0094636 A1 | 5/2004 | Channer | |
| 2004/0135000 A1 | 7/2004 | Buthier | |
| 2004/0262418 A1 | 12/2004 | Smith et al. | |
| 2004/0262421 A1 | 12/2004 | Hurry et al. | |
| 2005/0001337 A1 | 1/2005 | Pankhurst et al. | |
| 2005/0103880 A1 | 5/2005 | Taite | |
| 2005/0145711 A1 | 7/2005 | Blondeau et al. | |
| 2005/0196571 A1 | 9/2005 | Penny et al. | |
| 2006/0000920 A1 | 1/2006 | Leonard | |
| 2006/0083709 A1 * | 4/2006 | Hutchings et al. | 424/76.1 |

FOREIGN PATENT DOCUMENTS

| | | |
|---|---|---|
| EP | 1 346 734 | 9/2003 |
| GB | 2 254 558 | 10/1992 |
| GB | 3003643 | 11/2002 |
| GB | 3003644 | 6/2003 |
| GB | 3005517 | 7/2003 |
| GB | 3007046 | 9/2003 |
| GB | 3007049 | 9/2003 |
| GB | 3007052 | 9/2003 |
| GB | 3007053 | 9/2003 |
| GB | 3007054 | 9/2003 |
| GB | 3007055 | 9/2003 |
| GB | 3007056 | 9/2003 |
| GB | 3007057 | 9/2003 |
| GB | 3007233 | 9/2003 |
| GB | 3007045 | 10/2003 |
| GB | 3012024 | 2/2004 |
| GB | 3012025 | 2/2004 |
| GB | 3012026 | 2/2004 |
| GB | 3007048 | 10/2005 |
| JP | HA05015803 | 8/1993 |
| JP | 8-241039 | 9/1996 |
| JP | 9-84863 | 3/1997 |
| JP | D1027932 | 9/1998 |
| JP | 10-263068 | 10/1998 |
| JP | 1027932 | 10/1998 |
| JP | 1195937 | 2/2004 |
| JP | D1195937 | 2/2004 |
| NL | 000194709-0001 | 9/2004 |
| NL | 000205661-0001 | 10/2004 |
| NL | 000252358-0001 | 2/2005 |
| NL | 000252366-0001 | 2/2005 |
| WO | WO 96/33605 | 10/1996 |
| WO | WO 00/23121 | 4/2000 |
| WO | WO 03/068276 | 8/2003 |

OTHER PUBLICATIONS http://www.glade.com/plugins.asp.
http://www.airwick.us/product_page/product.html.
http://www.racerwheel.com/tcr-cz-103.html.
http://www.racerwheel.corn/tcr-cz-102a.html.
http://www.giftsandgadgetsonline.com/ioairfrwilif.html.
http://www.allproducts.com/gift/sundeal/02-ac105.html.
http://us.shop.com/cc.amos?main=catalog&pcd=783942&adtg=05180436&GA=1.
http://www.autobarn.net/skulrotairfr.html?AID=10274001&PID=613288.
http://www.negativeiongenerators.com/XJ-201ionicfreshener.html.
http://www.buylighting.com/Odor_eliminating light bulbs.html.
International Search Report in PCT/US2007/001568 dated Jun. 29, 2007.
International Search Report and Written Opinion in PCT/US2007/008035 dated Aug. 2, 2007.

* cited by examiner

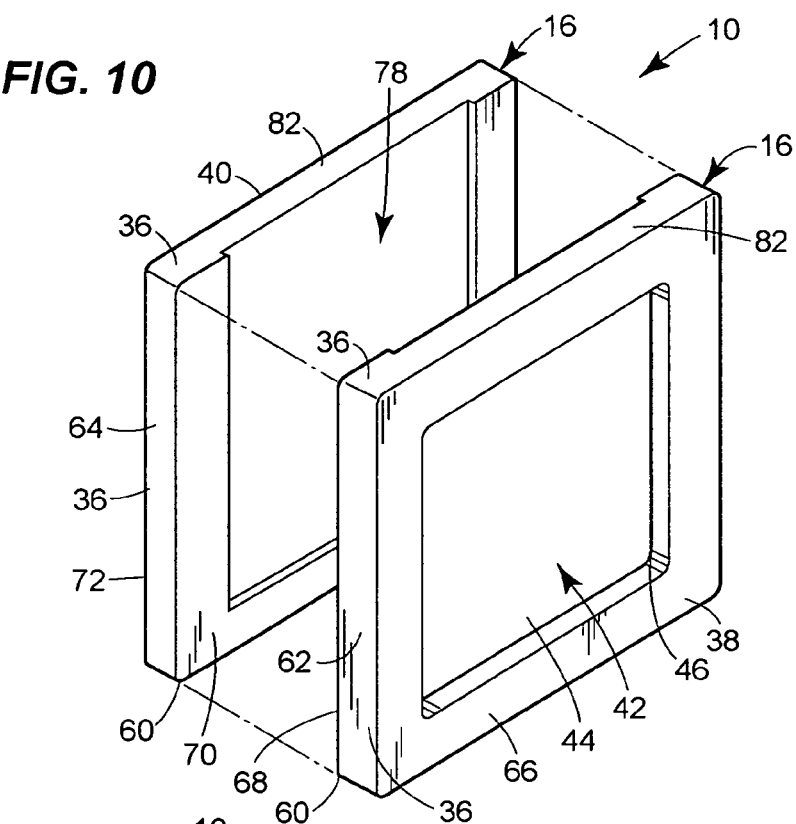
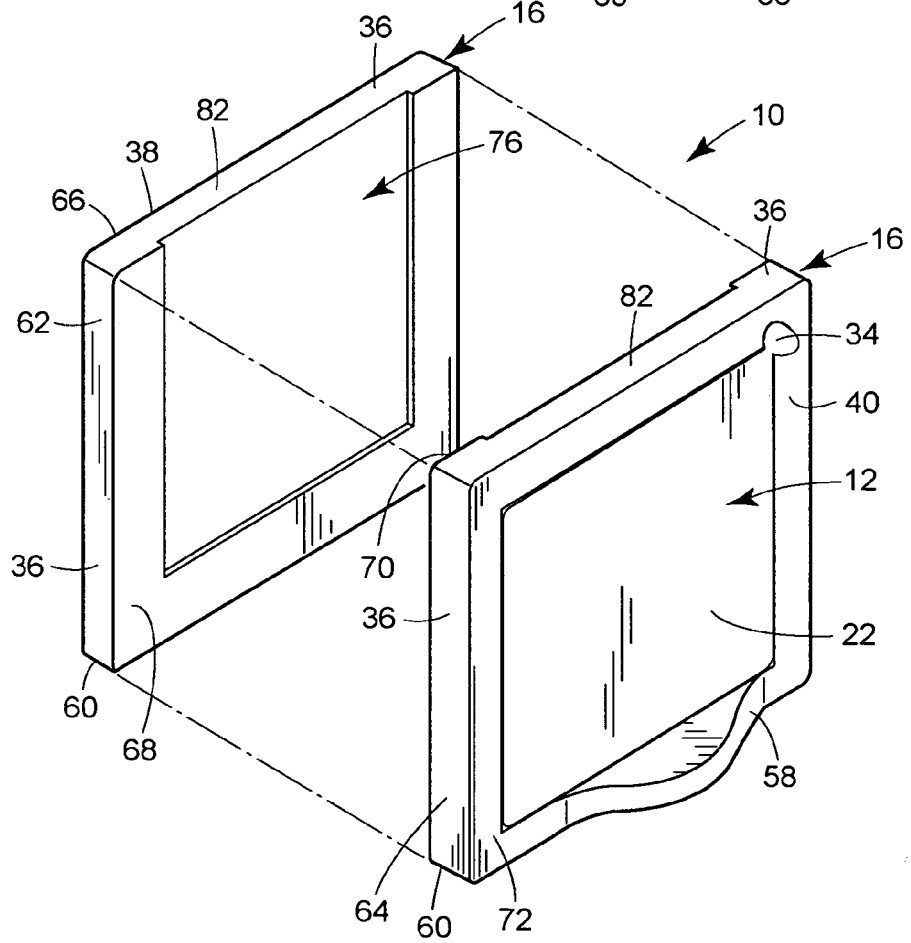

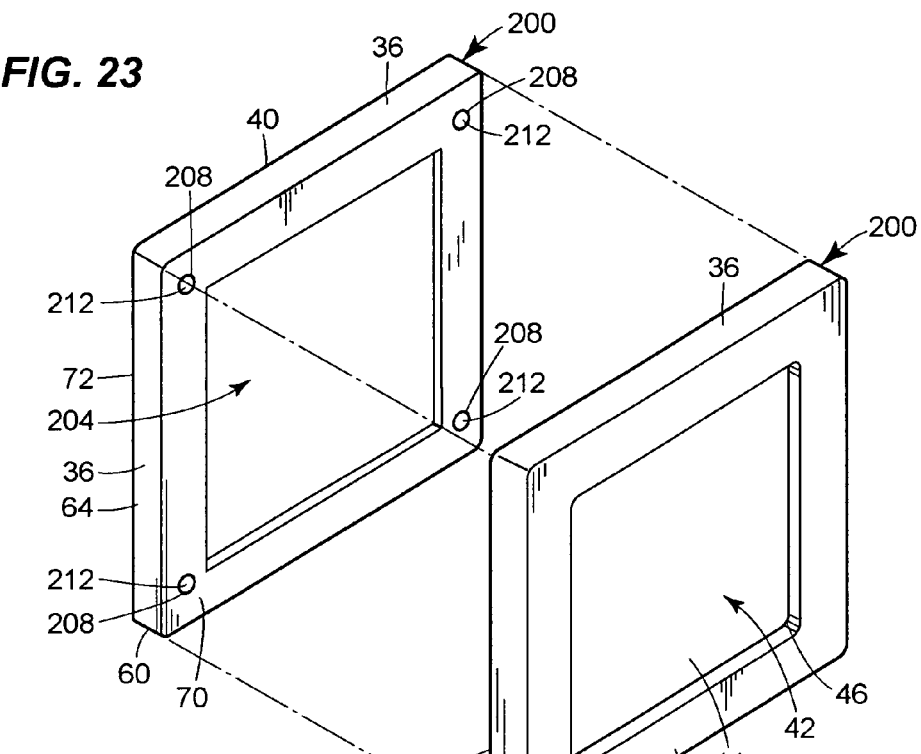
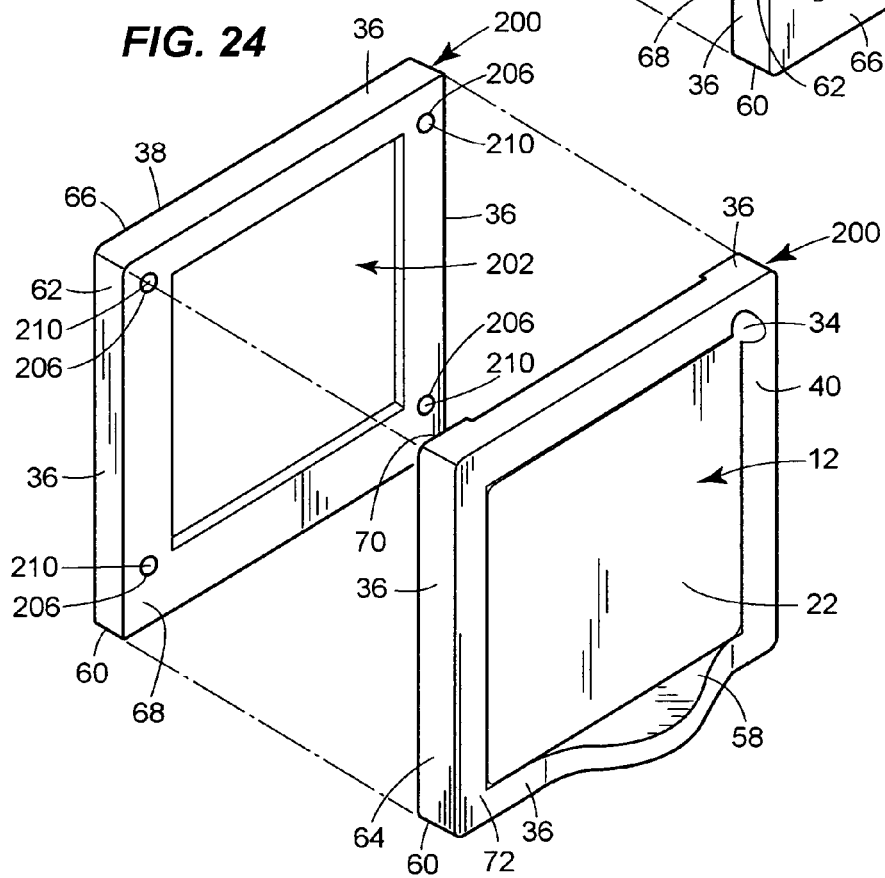

AIR FRESHENER WITH PICTURE FRAME

CROSS REFERENCE TO RELATED APPLICATIONS

This application is a continuation-in-part of application Ser. Nos. 10/880,634, now U.S. Pat. No. 7,188,780 Ser. No. 10/881,816, now U.S. Pat. No. 7,213,770 and Ser. No. 10/880,885, now abandoned which were filed on Jun. 30, 2004. This application claims priority to all such previous applications, and such applications are hereby incorporated herein by reference in their entireties.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Background

The present invention generally relates to a volatile material dispenser, and more particularly, to a volatile material dispenser in combination with a picture frame.

2. Description of the Background

Volatile material dispensers have been used to provide fragrances to office or home settings. One such dispenser is an ornamental design for a combination picture frame and air freshener receptacle. The picture frame is rectangular and has a bottom wall, a top wall, and two side walls. One of the side walls has a slot. An opening extends through a front face of the receptacle. A rear face of the picture frame is provided with an apertured receptacle. The receptacle has side portions that extend outwardly from the rear face of the picture frame and inwardly toward each other. The side portions are inwardly spaced from the side walls and are connected by a planar rear portion.

Another dispenser is an air freshener support for a car with a rectangular housing having a front panel with a rectangular opening disposed therein. A photograph is nested adjacent the opening so that peripheral edges of the photograph are adjacent inner portions of the front panel. A back cover is disposed behind the photograph so as to press and retain same between the front panel and the back cover. A rectangular pad impregnated with a fragrance is disposed adjacent the back cover.

Yet another dispenser is an air freshener picture frame with a rectangular housing having front and rear faces, wherein the front face has a front panel with a rectangular front opening therein, and the rear face has a rear opening. A back panel is disposed within the rear face and presses against a clear sheet and artwork to keep both in place within the rear face. An air freshener material is provided within an enclosure attached to a back side of the back panel, wherein the enclosure has vents to allow diffusion of a fragrance from the material.

SUMMARY OF THE INVENTION

According to one embodiment of the present invention, a picture frame comprises a frame having front and rear faces. A recess is disposed within the rear face of the frame. A dispenser is disposed within the recess of the rear face. The dispenser includes a reservoir and a vapor permeable membrane. A slot is disposed in a side wall of the frame and is configured to hold an image.

According to another embodiment of the present invention, a picture frame comprises a frame comprising a front block and a rear block. Both blocks include front and rear faces and the rear face of the front block is attached to the front face of the rear block. A recess is disposed in at least one of the rear face of the front block and the front face of the rear block that defines a slot. An additional recess is disposed in the rear face of the rear block. A dispenser is disposed within the recess in the rear face of the rear block. The dispenser includes a reservoir and a vapor permeable membrane.

According to yet another embodiment of the present invention, a picture frame comprises a front block and a rear block, wherein both blocks include front and rear faces. A recess is disposed in at least one of the rear face of the front block and the front face of the rear block. An additional recess is disposed in the rear face of the rear block. Means for releasably securing and aligning the rear face of the front block with the front face of the rear block are provided. A dispenser is disposed within the additional recess in the rear face of the rear block. The dispenser includes a reservoir and a vapor permeable membrane.

BRIEF DESCRIPTION OF THE DRAWINGS

Other aspects and advantages of the present invention will become apparent upon reading the following detailed description and upon reference to the drawings in which:

FIG. 10 is an exploded front isometric view of front and rear blocks comprising the frame;

FIG. 11 is an exploded rear isometric view of the frame of FIG. 10;

FIG. 23 is an exploded front isometric view of a sixth embodiment of the dispensing system showing separated front and rear blocks of a frame;

FIG. 24 is an exploded rear isometric view of the dispensing system of FIG. 23 showing separated front and rear blocks of the frame.

DETAILED DESCRIPTION OF THE INVENTION

Figure 1:
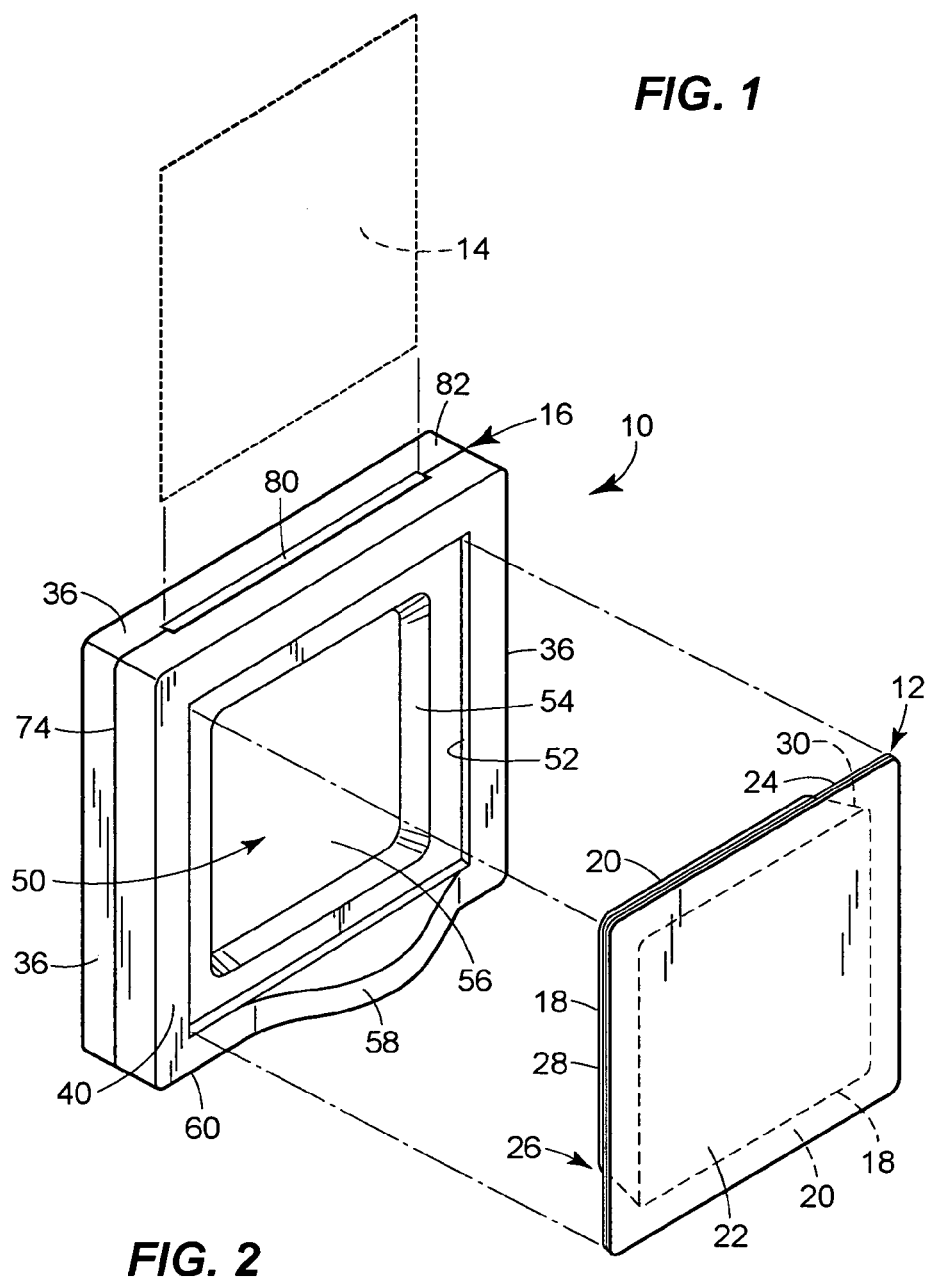
FIG. 1 is an exploded rear isometric view of the volatile material dispensing system that includes a frame, a dispenser, and an image.
Figure 2:
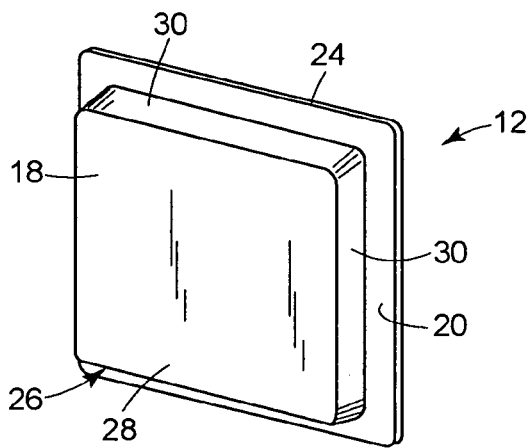
FIG. 2 is an isometric view of the dispenser as shown in FIG. 1.

Referring to FIGS. 1-11, a volatile material dispensing system 10 is illustrated. The dispensing system 10 includes a volatile material dispenser 12, an image 14, and a display frame 16 for holding the dispenser 12 and the image 14.

With particular reference to FIGS. 1, 2, and 7-9, the dispenser 12 includes a blister 18, a peripheral flange 20, and an impermeable laminate 22 releasably adhered to the blister 18 and flange 20. The blister 18 includes a non-porous permeable membrane 24 and a cup-shaped structure 26. The cup-shaped structure 26 includes a bottom wall 28 and four side walls 30 that in conjunction with the membrane 24 acts as a sealed reservoir to contain a volatile material 32.

The cup-shaped structure 26 may be comprised of a recycled polyethylene terephthalate (RPET) layer adhesively bonded to a nylon laminate. The nylon laminate may also include a layer of ethylene vinyl acetate (EVA) coextruded to each side of a middle nylon layer. The nylon laminate and RPET layer of the cup-shaped structure 26 in one embodiment have a thickness of about 0.3 to 0.4 mm. The cup-shaped structure 26 is generally rectangular and/or square with overall dimensions of about 3 to 5 mm high, about 50 to 60 mm long, and about 50 to 60 mm wide. Each of the cup-shaped structure's 26 four side walls 30 has a corresponding height of about 3 to 5 mm and a width of about 50 to 60 mm. Side walls 30 taper slightly outward as one moves from the bottom wall 28 to the flange 20. Bottom wall 28 is also generally rectangular and has a length of about 48 to 58 mm and a width of about 48 to 58 mm. The side walls 30 and bottom wall 28 of the cup-like structure 26 in one embodiment are thermoformed from a single sheet of the RPET and nylon laminate that is heated, then blown and/or pressed into the flange-and-cup arrangement shown in FIG. 2. The cup-shaped structure 26 may be clear and translucent, allowing for the visibility of the volatile material 32 contained within the blister 18.

Peripheral flange 20 is planar. It is coupled to and extends outward from the top edges of the cup-shaped structure 26 (e.g. upper edges of side walls 30). Flange 20 is integrally formed with the cup-shaped structure 26 in, for example, a thermoforming process, as described in the previous paragraph.

Figure 7:
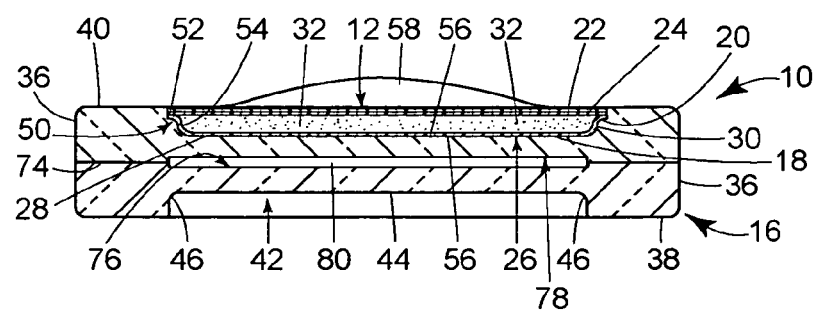
FIG. 7 is a sectional view of the dispensing system taken along the line 7-7 of FIG. 4.
Figure 8:
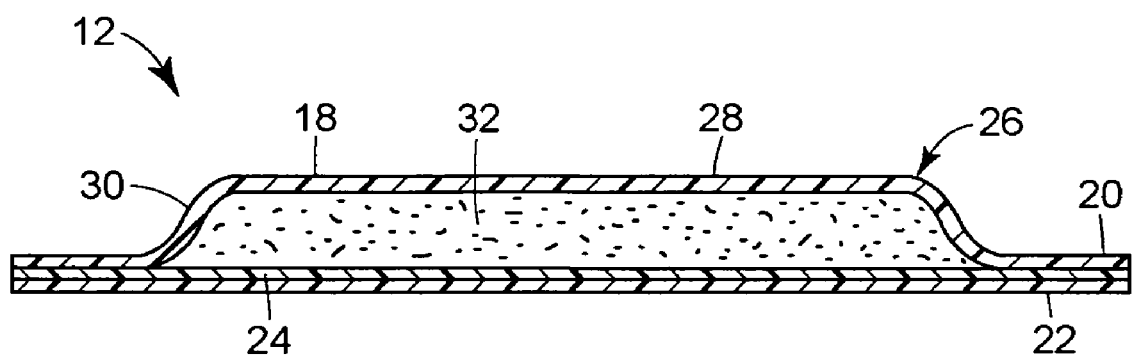
FIG. 8 is a partial enlarged sectional view of the dispenser as shown in FIG. 7 in a filled condition.
Figure 9:
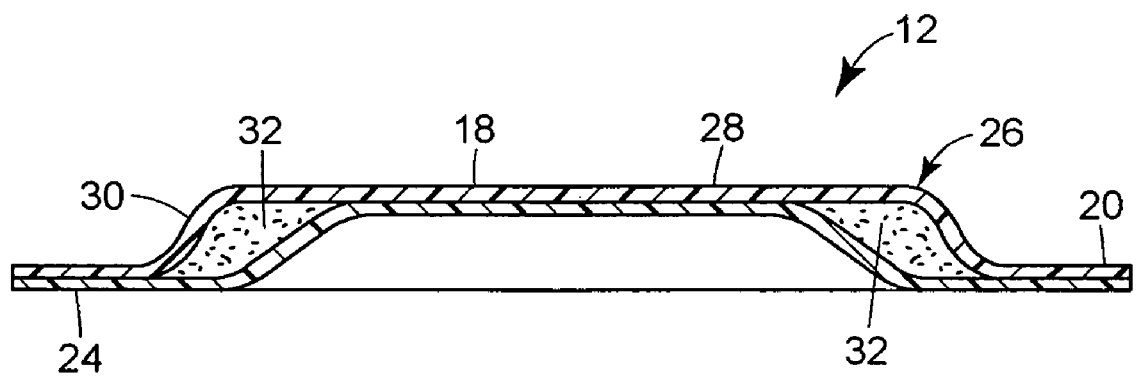
FIG. 9 is a partial enlarged sectional view of the dispenser as shown in FIG. 7 in an unfilled condition.

Illustratively, the permeable membrane 24 has a thickness of about 0.05 to 0.15 mm and has a density within a range of about 0.88 to 0.95 grams/cubic centimeter. Membrane 24 may also be formed integrally with laminate 22 and is heat fused to flange 20 such that membrane 24 extends across the entire cup-shaped structure 26. FIGS. 7 and 8 show membrane 24 enclosing and sealing the cup 26 with the volatile material 32 stored inside, thereby forming a thin sealed container impermeable to the volatile material 32 stored inside. This container remains substantially impermeable until the user grasps a corner of laminate 22 and peels laminate 22 from the membrane 24, thereby exposing permeable membrane 24 and permitting the volatile material 32 to migrate through the permeable membrane 24 and diffuse into the ambient air (FIG. 9). The membrane 24 is comprised of low density polyethylene (LDPE) and is clear and translucent, allowing for visibility of the volatile material 32 contained within the blister 18.

The laminate 22 may include a layer of polypropylene, aluminum foil, and/or polyester. The polypropylene may be adhesively bonded to the aluminum foil layer, which may be adhesively bonded to the polyester layer. An extrusion bonding material may be used to bond the layers together. Illustratively, laminate 22 has a thickness of between 0.1 and 0.2 mm. The polyester layer is generally suitable for printing and may be the outer surface of laminate 22.

Following placement of the volatile material 32 into the cup 26, a seal is made between the flange 20 and the permeable membrane 24 thereby forming the dispenser 12. As noted above, the laminate 22 may be attached to the blister 18 at the same time as the permeable membrane 24 if the laminate 22 and membrane 24 are co-extruded. The membrane 24 and laminate 22 may be attached to the flange 20 of the blister 18 using any conventional means, such as an adhesive, heat sealing, and/or crimping, or the like. The seal is substantially air-tight so as to prevent leakage of air or the volatile material 32. The volatile material 32 does not completely fill the void within the blister 18. A relatively small amount of air can be tolerated in the dispenser 12 following the creation of blister 18. For example, the air in the sealed blister is no more that 3-6% of the overall volume of the blister 18. As the volatile material diffuses out of dispenser 12 little or no air enters the blister 18 through the permeable membrane 24. In one embodiment, the membrane 24 is configured to distend and collapse with relatively few or no gas bubbles being formed.

There is substantially no diffusion of volatile material 32 when the dispenser is filled and laminate 22 covers membrane 24. Illustratively, the laminate 22 is removed from the blister 18 by a user grasping an end of the laminate 22 and peeling it off the blister 18. A tab 34, extension, or other means for grasping may be included as an extension of the laminate 22 to aid in removal of same. The extension may be at the corners, ends, and/or on the surface of the laminate 22.

Following removal of laminate 22, the system 10 begins to transition from a full or first condition (FIGS. 7 and 8) to an empty or second condition (FIG. 9). There may be a small amount of volatile material 32 that remains in the blister 18 and the dispenser 12 will still be considered to have reached the second condition. As the volatile material 32 diffuses through the membrane 24, the membrane 24 slowly collapses upon the bottom wall 28. With reference to FIG. 9, following diffusion of the volatile material 32 across the membrane 24 there is less material 32 contained within the dispenser 12. Substantially no new air enters the dispenser 12 subsequent to diffusion of the volatile material 32. The result of this is a pressure gradient across the membrane 24, with a higher pressure existing in the ambient air than the pressure in the dispenser 12. The pressure gradient causes the ambient air to exert a net positive pressure upon the dispenser, which presses the membrane 24 against the remaining volatile material 32 and ultimately the bottom wall 28. Continued diffusion of the volatile material 32 increases the force exerted upon the membrane 24, which causes the remaining volatile material 32 to migrate from a center of wall 28 toward a periphery of wall 28. Continued migration and diffusion of the volatile material 32 results in an increasing surface area contact between membrane 24 and wall 28 until dispenser 12 is empty, or nearly empty. The pressure gradient ultimately resulting in migration of the volatile material 32 may also be viewed as occurring due to an increasing compressed vacuum presence within dispenser 12 as the volatile material continues to diffuse across membrane 24.

A small amount of volatile material 32 may remain within the dispenser 12 when it is nearly empty, and present in the form of a ring-like appearance towards the periphery of the bottom wall 28. In one embodiment a dye and thickener combine to comprise approximately 2% of the overall volatile material composition of the system 10 at the first condition. A higher composition of dye is present in the volatile material 32 when the dispenser 12 is nearly empty, as the dye utilized does not easily diffuse across membrane 24. This results in a more readily viewable ring-like appearance. The color of the ring-like image is a more intense color than the coloration of the first condition because of the increased concentration of dye material. In the second condition the thickener and dye comprise nearly all of the material left within the dispenser 12. Of course, this may change dependent upon the particular dye composition and thickening agent utilized in the volatile material 32.

Figure 3:
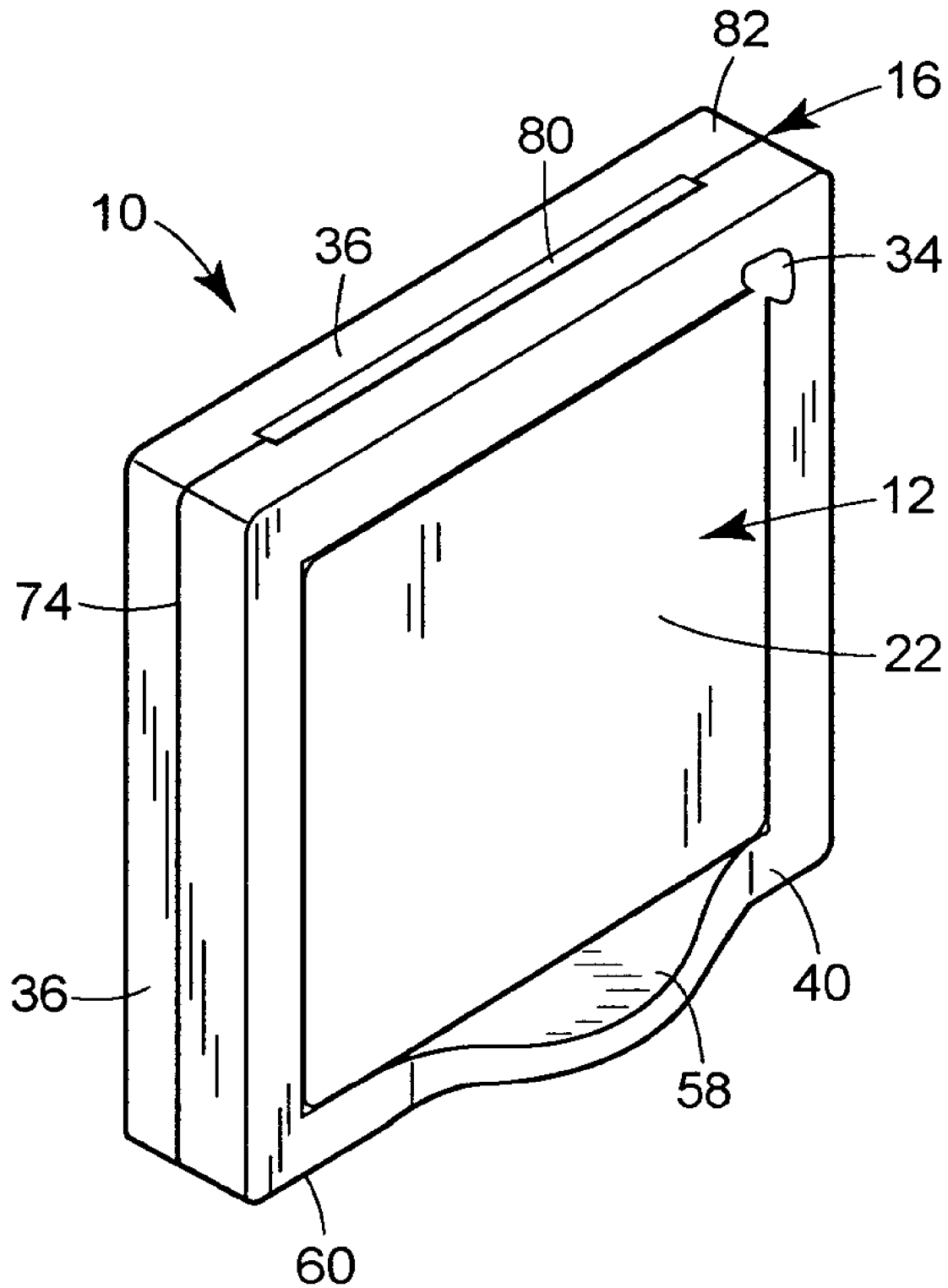
FIG. 3 is a rear isometric view of the assembled dispensing system shown in FIG. 1.
Figure 4:
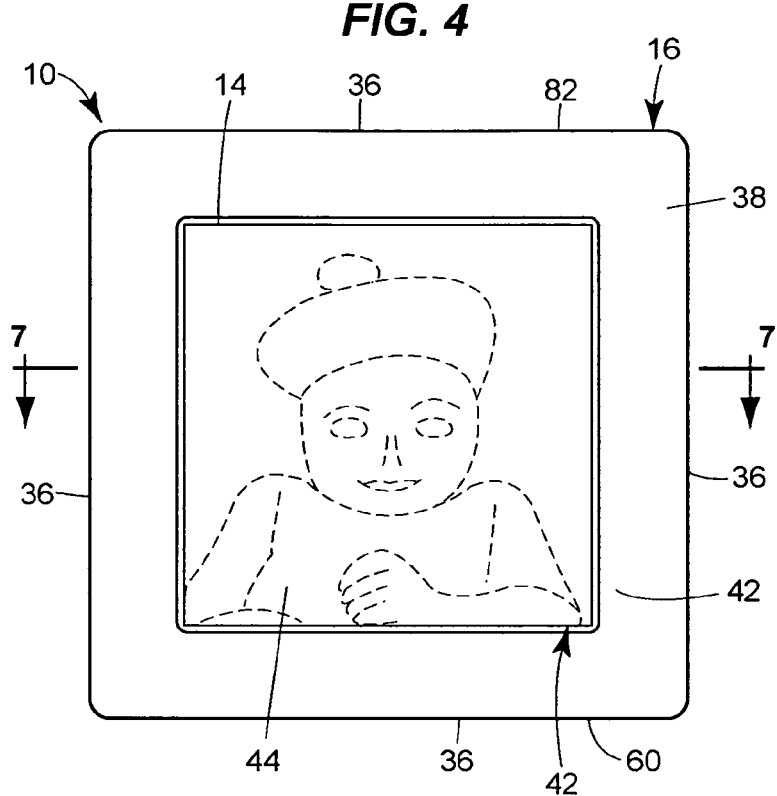
FIG. 4 is a front elevational view of the dispensing system of FIG. 3.
Figure 5:
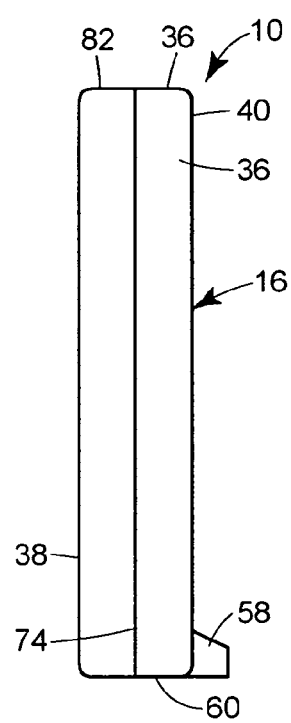
FIG. 5 is a side elevational view of the dispensing system of FIG. 3.
Figure 6:
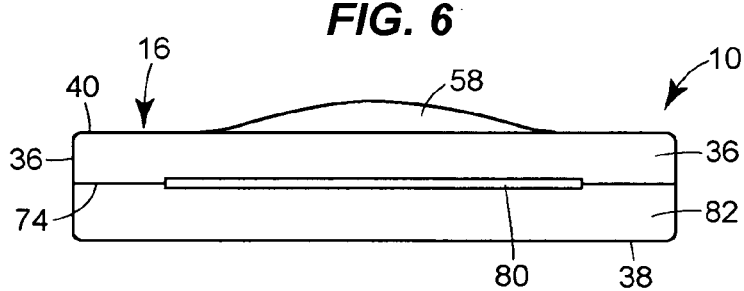
FIG. 6 is a plan view of the dispensing system of FIG. 3.

Frame 16 is a rectangular structure with four substantially equal-sized side walls 36 (FIGS. 1, 3, 5, and 6), a front face 38 (FIG. 4), and a rear face 40 (FIGS. 1 and 3). In one embodiment, frame 16 has a thickness within a range of about 12 to 22 mm and a height and width within a range of about 70 to 90 mm. In another embodiment, frame 16 has a thickness of about 16 mm and a height and width of about 86 mm. The front face 38 of frame 16 in one embodiment has a surface area greater than or equal to about 3000 mm$^2$.

Front face 38 includes a recess 42. The recess 42 is a square depression defined by four side walls and a bottom wall 44. Recess 42 gives frame 16 the appearance of a picture frame surrounding and framing the bottom wall 44 of the recess 42. FIG. 7, which shows a cross sectional view of the dispensing system 10, shows side walls defining the recess 42 having steps or curves 46 in the manner of an ornate picture frame. The recess 42 is centered in the front face 38 and is disposed away from the side walls 36. The front face 38 appears as a border extending around the edges that define recess 42, wherein the front face 38 has a constant width within a range of about 5 to 20 mm. In a different embodiment, the front face 38 may be planar and devoid of a recess. In yet another embodiment, a multiple stepped recess is provided. In any of the embodiments described herein, side walls defining the recesses may include curved and/or shaped walls. A raised rib 48 extends about an outer periphery of the front face 38 adjacent side walls 36 of the frame 16.

Rear face 40 of frame 16 includes a stepped recess 50 defined by stepped side walls and a square depression disposed therebetween. FIGS. 3 and 7 show that recess 50 is configured to completely receive dispenser 12, with dispenser 12 positioned so that the membrane 24 surface is substantially flush with rear face 40. Recess 50 includes a shallow peripheral recess 52 and a deep central recess 54. The central recess 54 is configured and dimensioned to receive the cup-shaped structure 26, and the peripheral recess 52 is configured and dimensioned to receive and support flange 20. The central recess 54 and peripheral recess 52 combined have a negative shape that is the same as that of dispenser 12.

Peripheral recess 52 in one embodiment has a mechanical and/or adhesive retaining means (not shown) that is configured to hold flange 20 in place. Flange 20 and the stepped side walls defining the peripheral recess 52 may be adhered to one another through the use of any adhesive, or alternately through a mechanical means, such as an interference fit, or a separate mechanical fastener, such as a spring clip. Further, a pair of magnets having opposing polarity could also be utilized to hold the flange 20 adjacent the stepped side walls of the peripheral recess 52. When an adhesive is used, a flange-to-frame adhesive may be chosen to either permanently adhere the flange 20 to the display frame 16 or, alternately, be releasably adhered for easy removal. In this manner, frame 16 can be a permanent and reusable item to which a succession of replacement dispensers 12 are affixed and later removed and replaced. An ultra violet (UV) cured adhesive may also be used.

As may be seen in FIG. 7, central recess 54 is deeper than peripheral recess 52 since it must accommodate the greater combined thickness of the cup-shaped structure 26, flange 20 and membrane 24. The bottom of the cup-shaped structure 26 is adjacent to and slightly spaced apart from a bottom 56 of central recess 54. Central recess 54 and peripheral recess 52 are centrally spaced from the edges of the rear face 40.

The rear face 40 of frame 16 also includes a curved foot 58 disposed adjacent a lower side 60 of the frame 16. The lower side 60 of the frame 16 is defined by one of the side walls 36 that rests against a support surface. The curved foot 58 increases the stability of the frame 16 to prevent same from tipping over. However, should the frame 16 be tipped over, the curved foot 58 causes the permeable membrane 34 to be spaced from the support surface so that the potential for damage to the support surface by the volatile material 32 is minimized. The curved foot 58 extends outwardly from the rear face 40 about 4 to 5 mm at its farthest point.

With particular reference to FIGS. 10 and 11, it is shown that the frame 16 is formed by bonding front and rear blocks 62, 64 together. The front block 62 includes a front panel 66 commensurate with the position and size of the front face 38 and a rear panel 68. Similarly, the rear block 64 includes a front panel 70 and a rear panel 72 commensurate with the position and size of the rear face 40. The front and rear blocks 62, 64 have length and width dimensions equal to about those of the frame 16. Further, the combined thickness of the front and rear blocks 62, 64 equals about the thickness of the frame 16. The rear panel 68 of the front block 62 is joined with the front panel 70 of the rear block 64 to make frame 16, wherein the front and rear blocks 62, 64 are joined at seam 74.

A first recess 76 is formed into the rear panel 68 of the front block 62. The recess 76 is defined by a rectangular depression that extends from one of the side walls 36 to an area adjacent an opposing side wall 36. Similarly, a second recess 78 is formed into the front panel 70 of the rear block 64 that is sized and aligned with the first recess 76. When the first and second blocks 62, 64 are joined, the first and second recesses 76, 78 are aligned with one another to form a single slot 80 configured to hold and/or display an image such as a photograph, a picture, and/or a drawing. Alternatively, a single recess having the same thickness as the combined first and second recesses 76, 78 may be formed in either the rear panel 68 of the front block 62 or the front panel 70 of the rear block 64. In this embodiment, the slot 80 is disposed on a top side 82 of the frame 16, wherein the top side 82 is defined by one of the side walls 36. Slot 80 defines a void having a height within a range of about 60 to 100 mm, a width within a range of about 50 to 80 mm, and a thickness within the range of about 1 to 5 mm. More particularly, the slot 80 is sized to allow any image 14 to be removably inserted therein by a user and may comprise any suitable height, width, and thickness proportions necessary to accommodate the image 14. For example, in one embodiment the slot may have a height and width within a range of about 10 to 500 mm, and more particularly within a range of about 20 to 250 mm, and most particularly within a range of about 40 to 125 mm.

The display frame 16 may be constructed from a variety of compositions, including glass, injection-molded plastic, and/or copolyester resin. Illustratively, the display frame 16 is constructed from molded glass that is clear and transparent. The image 14 is therefore viewable through the transparent front face 38 of the frame 16. Furthermore, if the image 14 is removed from slot 80, the cup-like structure 26 is viewable through the transparent front face 38. As noted above, the cup-like structure may be clear and translucent, allowing for the visibility of the volatile material 32 contained within the blister 18.

Figure 12:
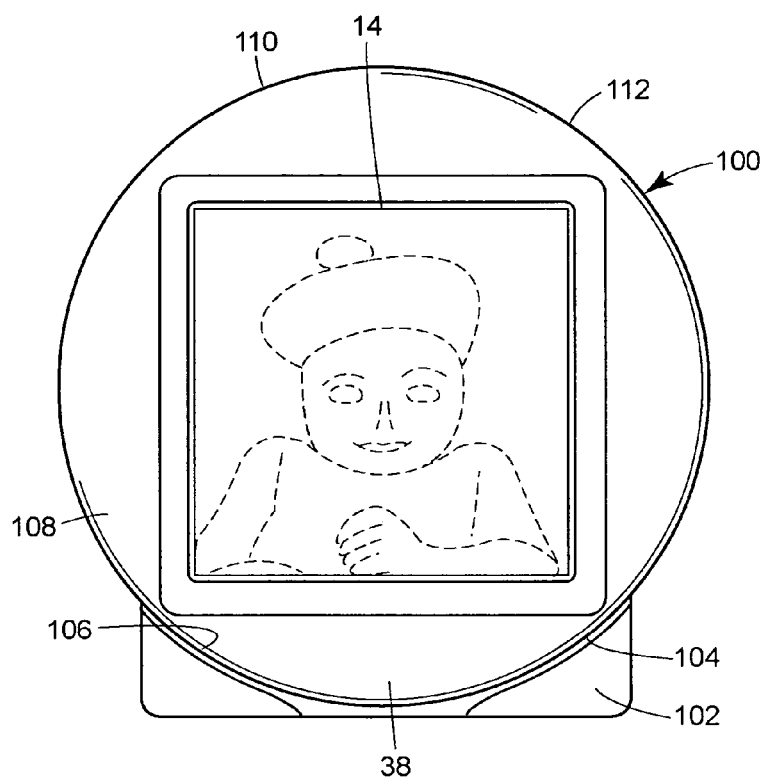
FIG. 12 is a front elevational view of a second embodiment of the dispensing system.
Figure 14:
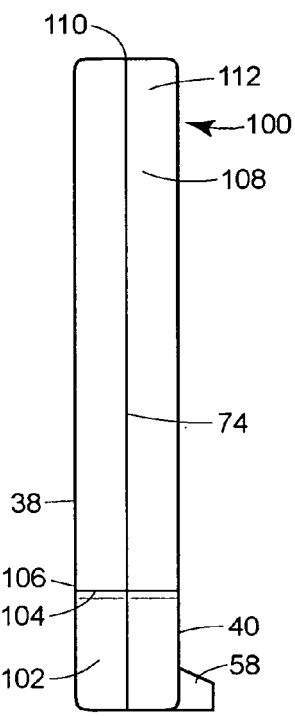
FIG. 14 is a side elevational view of the dispensing system of FIG. 12.
Figure 13:
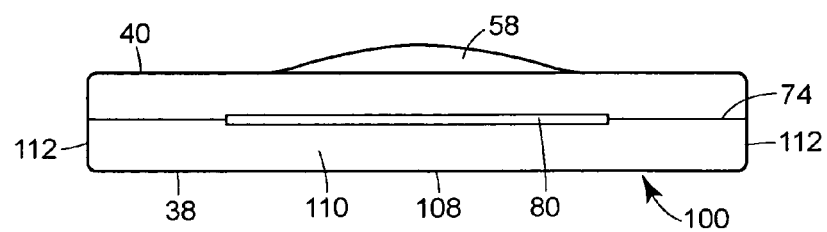
FIG. 13 is a plan view of the dispensing system of FIG. 12.

A second embodiment of the dispensing system 10 is depicted in FIGS. 12-14. The second embodiment is similar to the previously described first embodiment except that the second embodiment includes a frame 100 having a non-rectangular shape and a planar front face 38 devoid of the recess 42. Alternatively, the front face 38 of the present embodiment, and those discussed herein, may include a stepped recess disposed within the front face 38. Frame 100 includes a rectangular base 102 having a width of about 76 mm and a thickness of about 16 mm. The base 102 has a rounded recess 104 disposed on a top side thereof that is contoured to interfit with a lower portion 106 of a circular body 108. The circular body 108 is integral with the base 102 and has a diameter of about 102 mm. The combined height of the integral base 102 and body 108 is about 103 mm. The slot 80 is disposed in an upper portion 110 of a uniform side wall 112 spanning the distance between the front and rear faces 38, 40.

Figure 15:
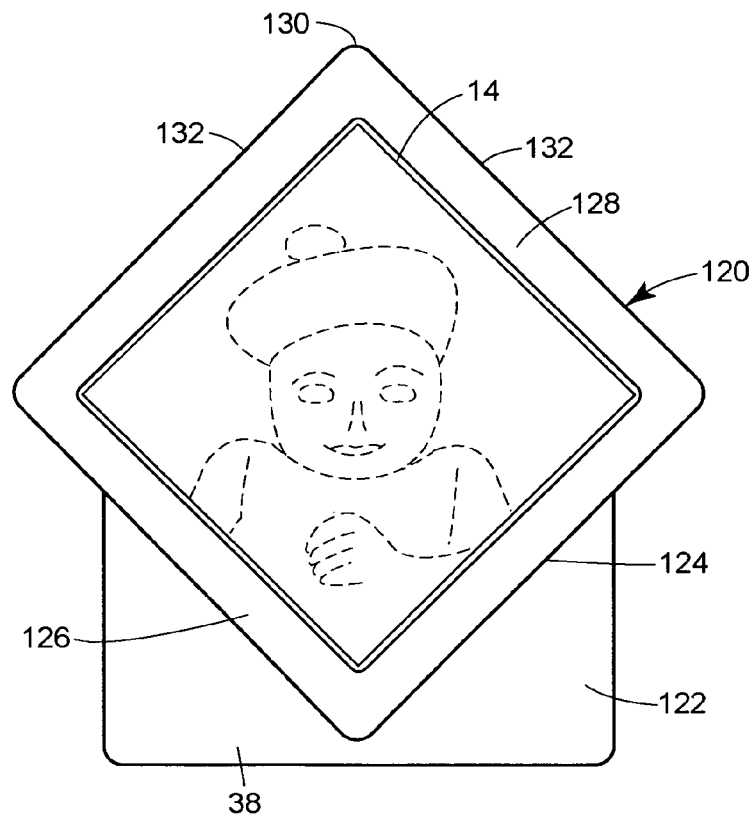
FIG. 15 is a front elevational view of a third embodiment of the dispensing system.
Figure 16:
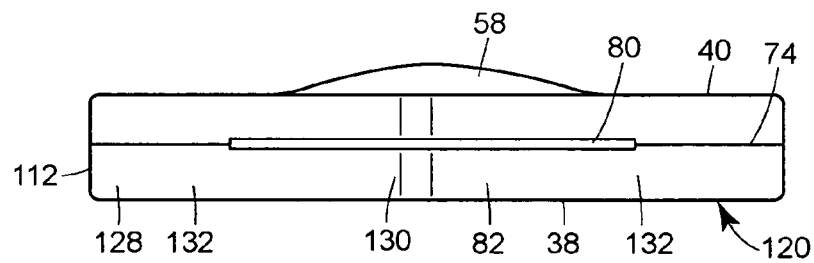
FIG. 16 is a plan view of the dispensing system of FIG. 15.
Figure 17:
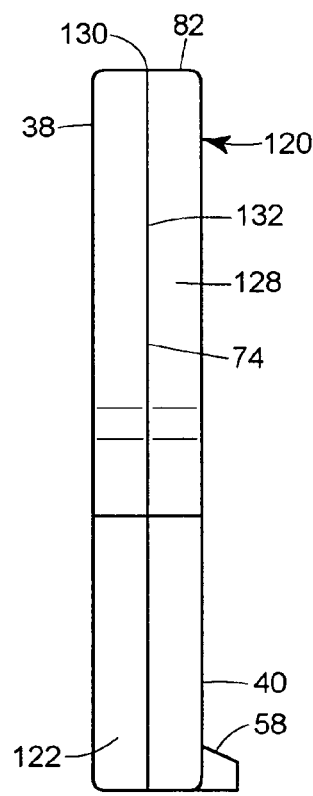
FIG. 17 is a side elevational view of the dispensing system of FIG. 15.

A third embodiment of the dispensing system 10 is depicted in FIGS. 15-17. Similar to the second embodiment, the third embodiment differs from the first embodiment only in that a frame 120 comprises a non-rectangular structure and has a planar front face 38 devoid of the recess 42. Frame 120 includes a rectangular base 122 having a width of about 76 mm and a thickness of about 16 mm. The base 122 has a triangular recess 124 disposed in a top side thereof that is contoured to interfit with a lower portion 126 of a diamond shaped body 128. The body 128 is integral with the base 122 and has a width (defined as the distance between opposing edges of the body 128) of about 103 mm. The combined height of the integral base 122 and the body 128 is about 107 mm. The slot 80 is disposed on an upper portion 130 that spans two side walls 132 of the frame 120.

Figure 18:
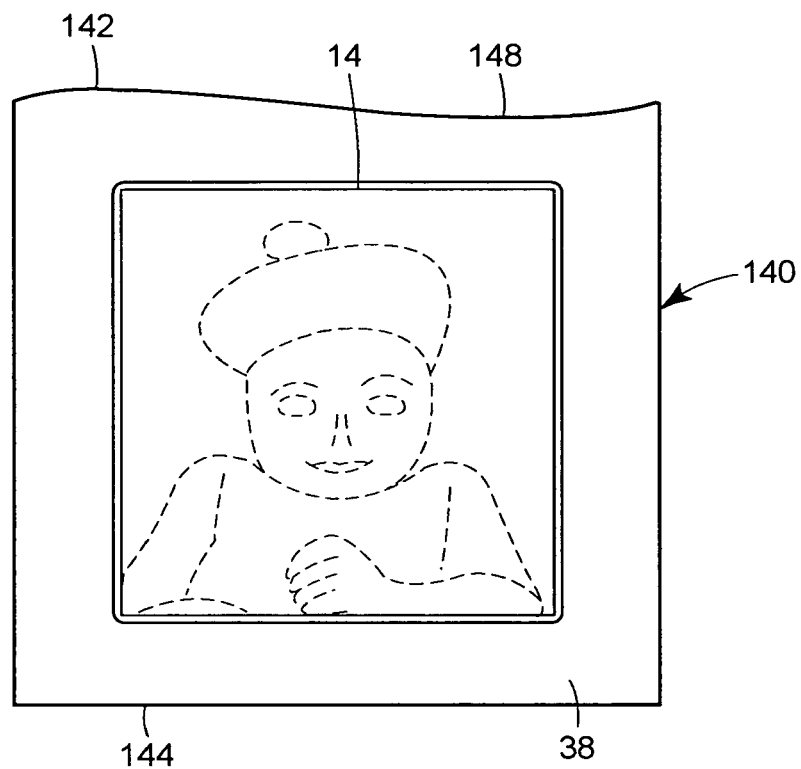
FIG. 18 is a front elevational view of a fourth embodiment of the dispensing system.
Figure 19:
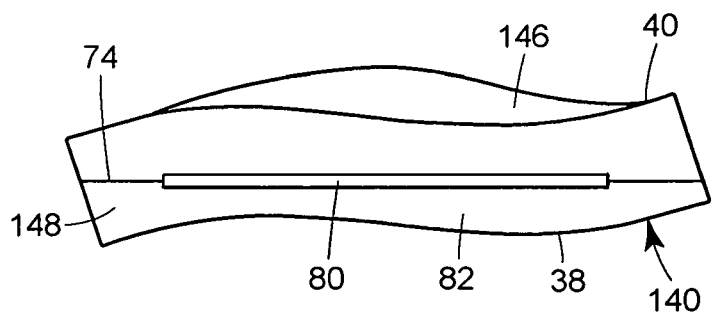
FIG. 19 is a plan view of the dispensing system of FIG. 18.
Figure 20:
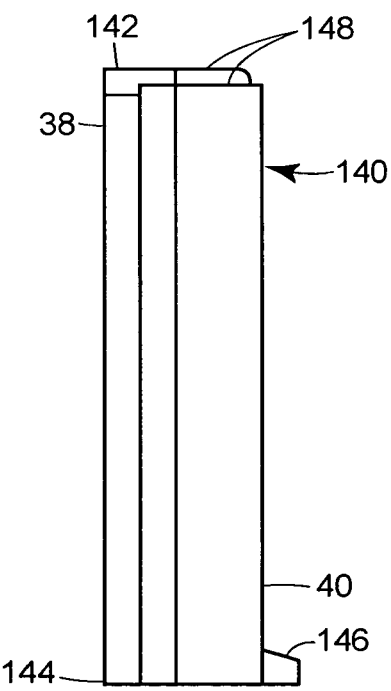
FIG. 20 is a side elevational view of the dispensing system of FIG. 18.

A fourth embodiment of the dispensing system 10 is shown in FIGS. 18-20 depicting a frame 140. The fourth embodiment differs from the first embodiment by way of having a non-rectangular frame 140 and a front face 38 devoid of the recess 42. The frame 140 comprises a wave-like shape. The wave-shaped frame 140 has a constant thickness of about 16 mm, but curves inwardly and outwardly throughout the approximate 85 mm width of the frame 140. The height of the frame 140 is not constant because an upper portion 142 thereof has a wave-shaped appearance. However, a peak height of the frame 140, measured from a lower portion 144 to the upper portion 142, is about 86 mm. Further, the frame 140 differs from the first embodiment in that frame 140 includes a wave-shaped foot 146 on the rear face 38 that differs from the curved foot 56 of the first embodiment. The combined thickness of the frame 140 and foot 146, measured between points that extend the farthest outwardly from both the front and rear faces 36, 38, is about 25 mm. The slot is disposed in a top side 148 of the frame 140.

Figure 21:
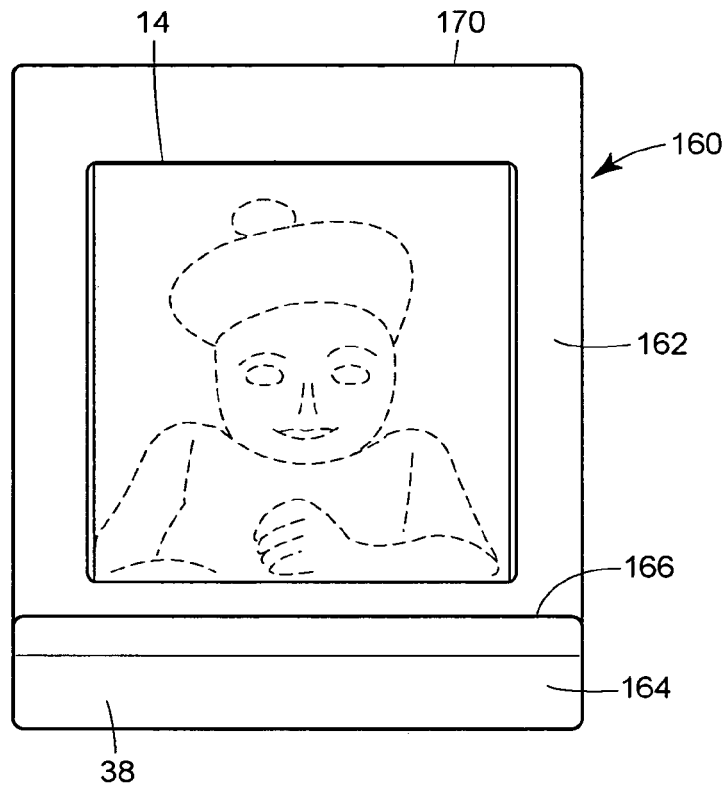
FIG. 21 is a front elevational view of a fifth embodiment of the dispensing system.
Figure 22:
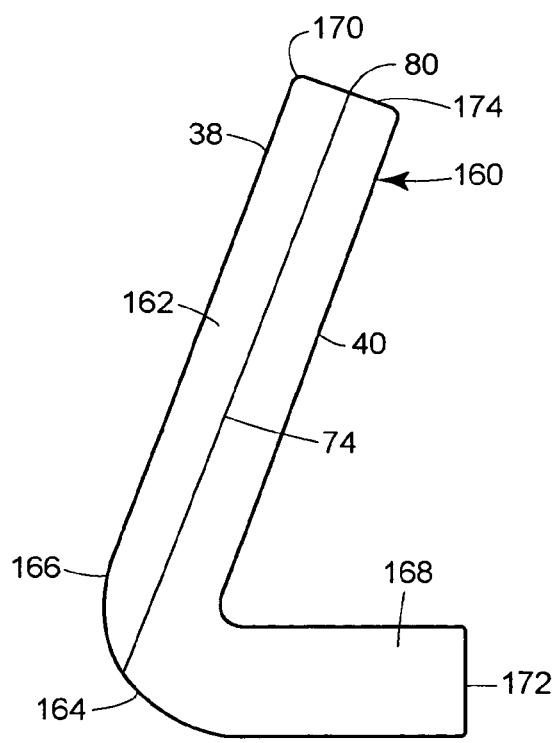
FIG. 22 is a side elevational view of the dispensing system of FIG. 21.

A fifth embodiment of the dispensing system 10 is shown in FIGS. 21 and 22 that differs from the first embodiment only with respect to the frame 16. The fifth embodiment includes a frame 160 that has a rectangular body 162. The body 162 is integrally connected to a curvilinear portion 164 on a lower portion 166 thereof. The curvilinear portion 164 is also integrally connected to a rectangular base 168. The body 162 is not perpendicular with respect to the base 168, but rather is deflected toward the base 168. The frame 160 has a width of about 80 mm and a height of about 96 mm, wherein the height is measured from the base 168 to an upper portion 170 of the body 162. The frame 160 has a thickness of about 51 mm, which is measured from an area of the curvilinear portion 164 adjacent the body 162 to an end 172 of the base 168. The slot 80 is disposed on a top side 174 of the frame 160.

Figure 25:
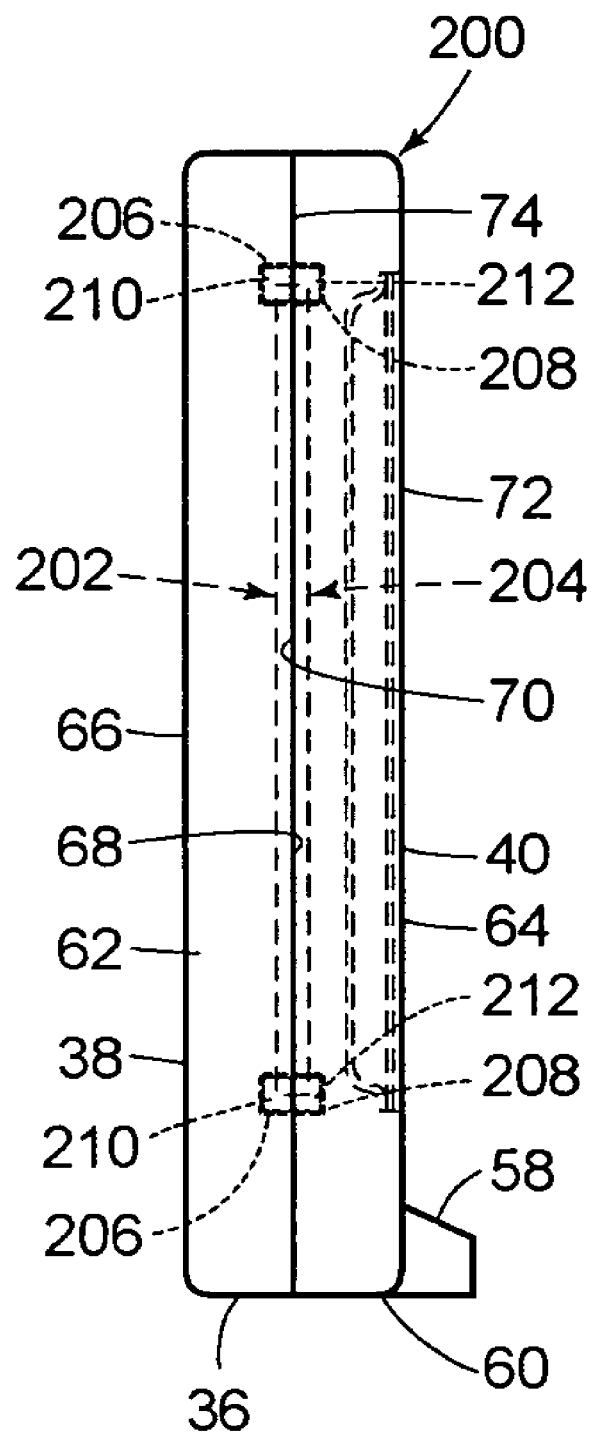
FIG. 25 is a side elevational view of the assembled dispensing system of FIG. 23.

Referring to FIGS. 23-25, a sixth embodiment of the volatile material dispensing system 10 that includes a frame 200 is illustrated. The present embodiment is similar to the first embodiment except that the frame 200 of the present embodiment does not have permanently bonded front and rear blocks 62, 64. Rather, the front and rear blocks are held together by removable attachment means such as a mechanical fastener, an adhesive, and/or magnets.

FIGS. 23 and 24 depict the front block 62 with the front and rear panels 66, 68 and the rear block 64 with the front and rear panels 70, 72. Further, a first recess 202 is provided in the rear panel 68 of the front block 62 and a second recess 204 is provided in the front panel 70 of the rear block 64. Alternatively, a single recess having the same thickness as the combined first and second recesses 202, 204 may be formed in either the rear panel 68 of the front block 62 or the front panel 70 of the rear block 64. The first and second recesses 202, 204 are defined by centrally disposed rectangular depressions that do not extend to the outer periphery of the front and rear blocks 62, 64. The first and second recesses 202, 204 have length and width dimensions within the range of about 50 to 70 mm.

A circular depression 206 is disposed adjacent each corner of the rectangular recess 202 on the rear panel 68. Similarly, circular depressions 208 are provided at each corner of the second recess 204 on the front panel 70. Magnets 210, 212 are positioned within each of the circular depressions 206, 208, respectively. The magnets 210, 212 are retained within the circular depressions 206, 208 by means of an adhesive or could be press-fit in. The magnets 210, 212 include top portions that are substantially level with respect to the rear and front panels 68, 70. The magnets 210 on the rear panel 68 have an opposite polarity to the magnets 212 on the front panel 70.

The image 14 is inserted into either the first or second recess 202, 204 so that a side to be viewed is closer to the front face 36 of the frame 200. As may be seen in FIG. 25, the front and rear blocks 62, 64 are thereafter pressed together so as to align the front and rear recesses 202, 204 and the magnets 210, 212. The magnets 210, 212 retain the front and rear blocks 202, 204 together to form a unified frame 200 that may be easily separated to change the image 14.

INDUSTRIAL APPLICABILITY

The volatile material dispensing system described herein advantageously combines the functional and aesthetic characteristics of a picture frame with a fragrance dispenser. Thus, the use of one unit versus two individual units in a home or office setting may be avoided.

Numerous modifications will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

What is claimed is:

1. A picture frame, comprising:
   a frame having front and rear faces;
   a recess disposed within the rear face of the frame, wherein the recess includes a peripheral recess and a central recess;
   a dispenser disposed within the recess of the rear face, the dispenser including a reservoir and a vapor permeable membrane, wherein substantially all of the vapor permeable membrane is exposed to an ambient atmosphere; and
   a slot disposed in a side wall of the frame and configured to hold an image.

2. The picture frame of claim 1, wherein the slot has at least one of a height and a width within a range of about 50 mm to about 100 mm.

3. The picture frame of claim 1, wherein the slot has a thickness within a range of about 1 mm to about 5 mm.

4. The picture frame of claim 1, wherein the image is a photograph.

5. The picture frame of claim 1, wherein a protrusion extends outwardly from the rear face.

6. The picture frame of claim 1, wherein the frame comprises a base member for supporting the frame and a body.

7. The picture frame of claim 1, wherein the image substantially obstructs a view of the dispenser through the front face of the frame.

8. A picture frame comprising:
   a frame comprising a front block and a rear block, both blocks including front and rear faces, and the rear face of the front block is attached to the front face of the rear block;
   a first recess disposed in the rear face of the front block and a second recess disposed in the front face of the rear block, wherein the first and second recesses are similarly sized and aligned to define a slot, and an additional recess disposed in the rear face of the rear block; and
   a dispenser disposed within the recess in the rear face of the rear block, the dispenser including a reservoir and a vapor permeable membrane, and wherein substantially all of the vapor permeable membrane is exposed to an ambient atmosphere.

9. The picture frame of claim 8, wherein the slot has at least one of a height and a width within a range of about 50 mm to about 100 mm.

10. The picture frame of claim 8, wherein the slot has a thickness within a range of about 1 mm to about 5 mm.

11. The picture frame of claim 8, wherein a protrusion extends outwardly from the rear face.

12. The picture frame of claim 8, wherein the frame comprises a base member for supporting the frame and a body.

13. picture frame of claim 8, wherein the slot is sized to allow an image to be inserted therein.

14. The picture frame of claim 13, wherein the image substantially obstructs a view of the dispenser through the front face of the front block.

15. A picture frame comprising:
    a front block and a rear block, both blocks including front and rear faces;
    a recess disposed in at least one of the rear face of the front block and the front face of the rear block, and an additional recess disposed in the rear face of the rear block;
    means for releasably securing and aligning the rear face of the front block with the front face of the rear block; and
    a dispenser disposed within the additional recess in the rear face of the rear block, the dispenser including a reservoir and a vapor permeable membrane, and wherein the vapor permeable membrane is substantially flush with the rear face of the rear block and substantially all of the vapor permeable membrane is exposed to an ambient atmosphere.

16. The picture frame of claim 15, wherein the recess disposed in at least one of the rear face of the front block and the front face of the rear block defines a compartment having at least one of a height a width within a range of about 50 mm to about 100 mm.

17. The picture frame of claim 15, wherein the recess disposed in at least one of the rear face of the front block and the front face of the rear block defines a compartment having a thickness within a range of about 1 mm to about 5 mm.

18. The picture frame of claim 15, wherein the recess disposed in at least one of the rear face of the front block and the front face of the rear block defines a compartment sized to allow an image to be inserted therein.

19. The picture frame of claim 15, wherein the means for releasably securing and aligning the rear face of the front block with the front face of the rear block includes at least one pair of opposing magnets.

* * * * *